United States Patent [19]

Arcari et al.

[11] 4,223,146

[45] Sep. 16, 1980

[54] 4,5,6,7-TETRAHYDROIMIDAZO-[4,5-c]-PYRIDINE DERIVATIVES

[75] Inventors: Giuliana Arcari; Luigi Bernardi; Giovanni Falconi; Ugo Scarponi, all of Milan, Italy

[73] Assignee: Farmitalia Carlo Erba S.p.A., Milan, Italy

[21] Appl. No.: 959,506

[22] Filed: Nov. 13, 1978

[30] Foreign Application Priority Data

Aug. 7, 1978 [IT] Italy .................... 26562 A/78

[51] Int. Cl.² ............................................ C07D 471/04
[52] U.S. Cl. .................................... 546/118; 424/256
[58] Field of Search ......................................... 546/118

[56] References Cited

U.S. PATENT DOCUMENTS 4,141,899  2/1979  Arcari et al. .................... 546/118

Primary Examiner—Alan L. Rotman
Assistant Examiner—Natalia Harkaway

Attorney, Agent, or Firm—Stevens, Davis, Miller & Mosher

[57] ABSTRACT

Compounds are disclosed of the general formula (I):

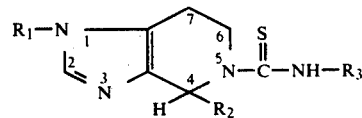

wherein $R_1$ is a lower alkyl having from 1 to 4 carbon atoms; $R_2$ is hydrogen or a lower alkyl having from 1 to 4 carbon atoms; and $R_3$ is a saturated or unsaturated straight or branched alkyl having from 1 to 4 carbon atoms. A process for making such compounds is also disclosed. These compounds are useful as antiulcer agents and as inhibitors of gastric secretion.

5 Claims, No Drawings

4,5,6,7-TETRAHYDROIMIDAZO-[4,5-c]-PYRIDINE DERIVATIVES

The present invention relates to new 4,5,6,7-tetrahydroimidazo-[4,5-c]-pyridine derivatives of general formula (I) and to a process for their preparation:

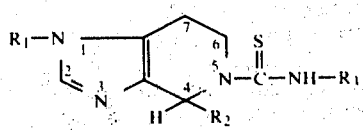

where R₁ is a lower alkyl having from 1 to 4 carbon atoms; R₂ is hydrogen or a lower alkyl having 1 to 4 carbon atoms; and R₃ is a saturated or unsaturated straight or branched alkyl having from 1 to 4 carbon atoms.

In a previous Belgian Pat. No. 850,130—cf. Arcari et al application Ser. No. 838,844 filed Oct. 3, 1977, and now U.S. Pat. No. 4,141,899—useful agents in the therapy of gastric and duodenal ulcers have been described which are 4,5,6,7-tetrahydroimidazo-[4,5-c]-pyridines of the general formula (II):

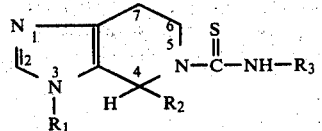

wherein the meaning of the R₁, R₂ and R₃ substituents are, among others, those given above for compounds of formula (I). These compounds were obtained by reacting substituted imidazo-[4,5-c]-pyridines (IV) with suitable N-alkyl isothiocyanates (V):

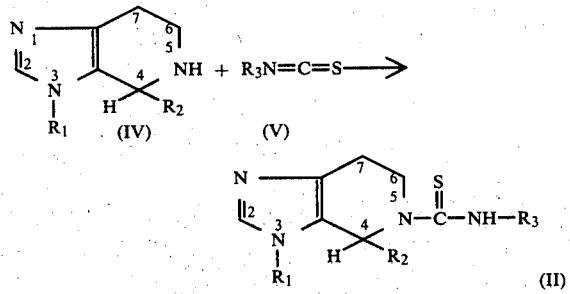

The starting 3,4-substituted imidazo-[4,5-c]-pyridines of formula (IV) were synthetized by alkylation of the 4-substituted or unsubstituted 4,5,6,7-tetrahydroimidazo-[4,5-c]-pyridines (VI) following the synthesis diagram:

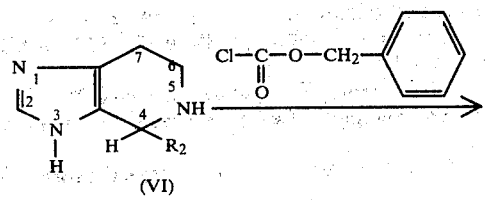

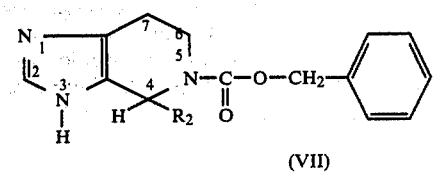

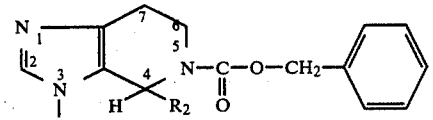

As the synthesis diagram shows, the compounds of formula (VI) were first reacted with benzyl chloroformate for protecting the secondary amino nitrogen atom and the so obtained protected derivatives of formula (VII), after metalation with strong organic bases such as n-butyl lithium or potassium ter-butylate, were successively alkylated using a suitable alkyl halide or dialkyl sulphate.

Chromatography of the alkylated product on silica gel yielded pure (VIII) as an oil, showing a single spot in TLC chromatography on silica gel plates.

The subsequent hydrogenolysis of the so obtained 3-alkylated compounds of formula (VIII), using palladium on carbon as catalyst or a treatment with 20% hydrobromic acid in acetic acid, afforded the desired intermediates of formula (IV), to be successively condensed with the alkyl isothiocyanates (V) to the final products of formula (II).

Later on, a careful examination of the first fractions resulting from the chromatography of the crude (VIII) showed the presence of a less polar substance, having a greater Rf in the system chloroform-methanol 9:1, which was isolated and shown to be the isomeric 1-alkyl derivative (VIII') from which the isomeric amine (IV') was obtained by hydrogenolysis or by treatment with 20% hydrobromic acid in acetic acid. Condensation of the isomeric amine (IV') with various alkyl isothiocianates afforded the final products of formula (I) which, surprisingly, showed enhanced pharmacological activity and very low toxicity in comparison with their isomeric products of formula (II).

It may be further pointed out that the new compounds (I) are clearly distinguishable from their isomeric 3-alkyl analogues (II), either by TLC because (I) always show an Rf greater than that of their isomeric analogues of formula (II) in the system chloroform:methanol 9:1, or by NMR spectrometry.

As a matter of fact, the proton or the methylene (if R₂=H) of the C-4, for compounds having the general formula (I), resonates at a higher magnetic field in comparison with the analogous compounds having the general formula (II).

Having found that the compounds of formula (I) had superior pharmacological properties, a new process was devised—and this is another object of the present invention—to obtain in a regiospecific way the 1-alkyl-4,5,6,7-tetrahydroimidazo-[4,5-c]-pyridines of general formula (IV'):

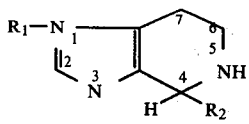

rather than the 3-alkyl-4,5,6,7-tetrahydroimidazo-[4,5-c]-pyridines of formula (IV) resulting from the previously described procedure. This is done as follows:

Using as starting material the compounds of formula (VII), the new alkylation step is now performed in a two-phase system benzene-aqueous sodium hydroxide 18 N, in the presence of a phase transfer catalyst such as n-tetrabutylammonium bromide, triethylbenzylammonium chloride or other quaternary alkyl ammonium salt (*Synthesis*, 441; 1973), by means of the usual alkylating agents (e.g., alkyl halides, alkyl p-toluene sulphonates, alkyl sulphates).

Under these conditions the alkylation step is highly regiospecific, giving rise, as the major product, to the 1-alkylated intermediates of formula (VIII') which, following the previous synthesis diagram, are successively transformed into the new compounds of this invention having the general formula (I):

Dai et al, *Eur. J. Pharm.*, 1975, 33, 277), was adopted as the reference standard.

(B 1) Inhibition of Restraint Ulcer in Rats (Bonfils et al, *Therapie*, 1960, 15, 1096).

Six Sprague - Dawley male rats (100–120 g) fasted for 24 hours were used for each group. A square flexible small-mesh wire netting was used for immobilization. After 4 hours immobilization the rats were sacrificed, their stomachs were removed, and lesions counted under a dissecting microscope.

The results obtained are reported below in Table 1, wherein the values are given as $ED_{50}$.

The compounds were administered subcutaneously (s.c.) immediately before the immobilization or orally (os) one hour before.

(2) Inhibition of Gastric Secretion in Rats (Shay, *Gastroenterology*, 1945, 43, 5).

Gastric antisecretory activity was evaluated in rats by the pylorus ligature technique. Six Sprague-Dawley male rats (110–130 g) were used for each group. Twenty-four hours before the test, the rats were deprived of food but their water supply was maintained. On the day of the operation, the pylorus was ligated under light ether anaesthesia. Four hours after the ligature, the rats were sacrificed, the stomach secretion was collected and centrifuged at 3500 r.p.m. for 10 minutes, and the volume, less sediment, was determined.

The amount of the free hydrochloric acid in the gastric juice was determined by titration against 0.01 N sodium hydroxide, using Topfer's Indicator. Each compound was injected subcutaneously at the time of liga-

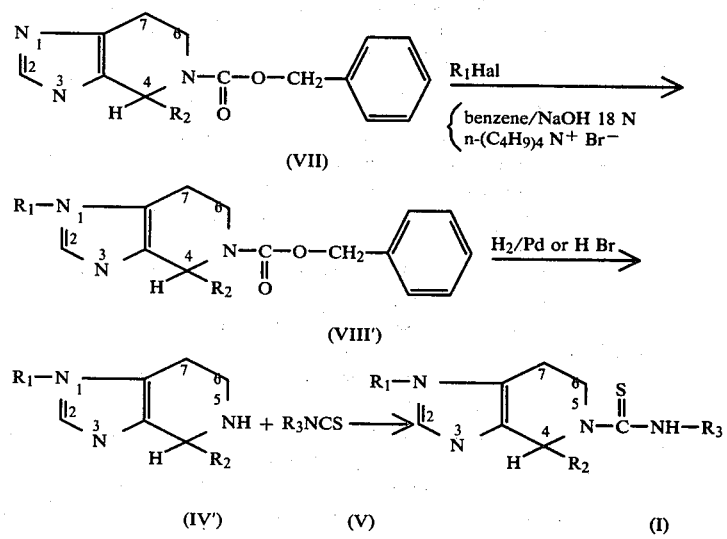

The yields of the final compounds of general formula (I) are as high as 70–75%.

The new compounds of formula (I), which may be isolated either as the free bases or as salts of the conventional pharmaceutically acceptable acids, display a higher pharmacological activity and minor toxicity in comparison with the previously described compounds of formula (II) in the therapy of gastric and duodenal ulcers. Thus, the activity of these compounds was assessed in rats in anti-ulcer and anti-secretory tests. Methiamide, which is well known for its antisecretory activity (Wyllie et al: *Gut*, 1973, 14, 424), and is considered one of the most active substances in this field (S.

ture.

The results are indicated in Table 1.

(3) Anticholinergic Activity in Rats.

Considering that many anti-ulcer agents display, as does atropine, a remarkable but undesired anti-cholinergic activity, some derivatives were assessed for their antagonism against chromodacryorrhea induced by carbacholine in rats. (Winburg M. et al, *J. Pharm. Exp. Therap.*, 1949, 95, 53).

From 3 to 5 Sprague-Dawley male rats, 250 g body weight, were employed for each group, following Winburg et al.

The Table 1 shows the results obtained expressed as $ED_{50}$.

Table 1

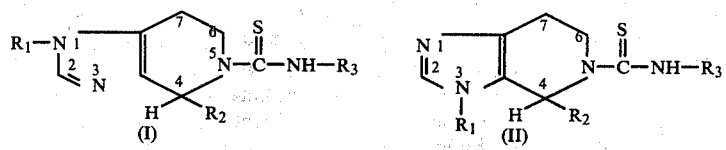

| Formula | $R_1$ | $R_2$ | $R_3$ | ED$_{50}$ (mg/Kg) in rats | | | | |
|---|---|---|---|---|---|---|---|---|
| | | | | Antiulcer | | Antisecretory | Anticholinergic | |
| | | | | s.c. | os | s.c. | s.c. | os |
| I | $CH_3$ | H | i.Pr | 1.2 | 4.5 | 26 | 25 | 100 |
| II | " | " | " | 0.85 | 8.5 | 34 | 7 | 50 |
| I | $C_2H_5$ | $C_2H_5$ | i.Pr | 2 | 3.5 | 6 | >200 | >400 |
| II | " | " | " | 3.5 | 4 | 10 | >100 | >100 |
| I | $CH_3$ | H | $CH_3$ | 15 | 25 | 30 | >100 | >100 |
| II | " | " | " | 50 | 50 | 50 | 50 | 100 |
| I | $CH_3$ | $C_2H_5$ | i.Pr | 4 | 2.5 | 20 | >100 | >100 |
| II | " | " | " | 10 | 50 | 50 | 40 | 60 |
| Methiamide | | | | 14 | 64 | 60 | 65 | 85 |

Four compounds were examined also for the activity on acetylsalicyclic acid- and cysteamine-induced ulcers and their toxicity was also determined in mice.

(4) Inhibition of Acetylsalicylic Acid-Induced Gastric Ulcers in Rats.

Six Sprague-Dawley male rats (200–250 g) were used for each group. Twenty-four hours before the test, the rats were deprived of food but their water supply was maintained. Acetylsalicylic acid (100 mg/Kg) suspended in 5% gum arabic solution was given orally to the rats. Antagonists, at 3 dose levels, were given orally 60 minutes, and subcutaneously 30 minutes, before the acetylsalicylic acid treatment.

After sacrificing the animals, four hours after administration of the antagonist, the stomachs were removed, slightly inflated and immersed in 1% formalin solution for 10 minutes for fixation.

Subsequently, the stomachs were incised along the greater curvature and the lengths of lesions measured under a dissecting microscope (10 X) with a square grid. The sum of the lengths (mm) of the lesions per rat was used as the ulcer index. The percentage inhibition was calculated in respect of the ulcer index of the control group.

The results are given below in Table 2.

(5) Inhibition of Cysteamine-Induced Duodenal Lesions in Rats.

Six Sprague-Dawley male rats (200–225 g) were used for each group. Twenty-four hours before the test, the rats were deprived of food but allowed free access to water. Cysteamine HCl (400 mg/Kg) dissolved in physiological saline was administered subcutaneously.

Antagonists were given orally 60 minutes, and subcutaneously 30 minutes, before the cysteamine treatment. The animals were kept fasting completely for 18–24 hours after cysteamine administration, then sacrificed by an overdose of ether.

The stomach and duodenum of each rat were excised to determine the presence of gastroduodenal lesions. The sum of the area (mm$^2$) of lesions for each rat was measured under a dissecting microscope (10X) with a square grid and then used as an ulcer index. The percentage inhibition was calculated in respect of the ulcer index of the control group.

The results of the tests are reported below in Table 2.

Table 2

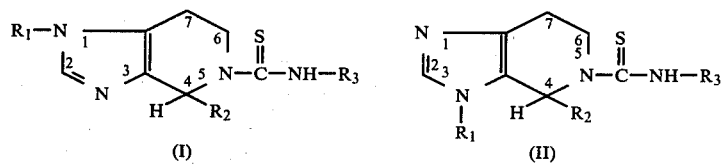

| Formula | $R_1$ | $R_2$ | $R_3$ | ED$_{50}$(mg/Kg) in rats | | | | LD$_{50}$ os (in mice) |
|---|---|---|---|---|---|---|---|---|
| | | | | Acetylsalicilic acid | | Cysteamine | | |
| | | | | s.c. | os | s.c. | os | |
| I | $C_2H_5$ | $C_2H_5$ | i.Pr | 0.7 | 0.7 | 0.5 | 10 | >2500 |
| II | " | " | " | 6.5 | 9 | 5.5 | 40 | 870 |
| I | $CH_3$ | " | " | 10 | 20 | 20 | 40 | >2500 |
| II | " | " | " | 25 | 40 | 50 | 100 | 980 |

From the data of Tables 1 and 2, it is evident that the compounds of the present invention having the general formula (I) have significantly higher antiulcer and antisecretory activities than those of the reference compound.

Moreover, the compounds having the 1-alkyl substituent (formula (I)) show higher activity both as antiulcer and antisecretory agent than the corresponding 3-alkyl derivatives (formula (II)).

It will also be noted that the anticholinergic activity, which is undesired since it is responsible for unpleasant side effects, is reduced in the 1-alkyl derivatives (formula (I)) in comparison to the 3-alkyl derivatives (formula (II)).

Finally, the comparison of the activities of the 1-alkyl and the 3-alkyl derivatives in the protection from acetylsalicylic acid- and cysteamine-induced ulcers (Table 2), shows that the 1-alkyl derivatives (formula (I)) are clearly superior to the corresponding 3-alkyl derivatives (formula (II)).

Last but not least, the 1-alkyl derivatives are less toxic than the 3-alkyl derivatives and therefore the therapeutic index is greatly superior.

EXAMPLE 1

1,4-Diethyl-5-(N-isopropylthiocarbamoyl)-4,5,6,7-tetrahydroimidazo-[4,5-c]-pyridine.

A mixture of 3.024 g of 4-ethyl-4,5,6,7-tetrahydroimidazo-[4,5-c]-pyridine (Farmaco, *Ed. Sci.*, 1967, 22, 821), 5.80 g of potassium carbonate, 30 ml of water, and 22 ml of chloroform is cooled with ice water and stirred vigorously.

A solution of 7.165 g of benzyl chloroformate in 30 ml of chloroform is added in about 8 hours.

The ice bath is then removed and the mixture is stirred overnight at room temperature. The organic layer is separated, dried, evaporated in vacuo and to an oily residue, dissolved in 60 ml of methanol, and 20 ml of 2N sodium hydroxide are added with stirring. After 1 hour the solution is neutralized and repeatedly extracted with chloroform. The combined extracts are dried, evaporated in vacuo, and the residue dissolved in 20 ml of 1N hydrochloric acid. The hydrochloric solution is successively evaporated to dryness and the residue is treated with 30 ml of a mixture of ethyl ether-ethyl acetate (95:5 v/v) to precipitate 4-ethyl-5-benzyloxy-carbonyl-4,5,6,7-tetrahydroimidazo-[4,5-c]-pyridine hydrochloride which is filtered and dried. 5.39 grams are obtained, melting at 162° C.

The hydrochloride is dissolved in 25 ml of water, whereupon the solution is neutralized and extracted repeatedly with chloroform. The combined extracts are dried, evaporated in vacuo, and the oily residue dissolved in 72 ml of benzene. To this solution 10.8 ml of 18N sodium hydroxide are added with stirring. To the resulting mixture, 0.468 g of n-tetrabutyl-ammonium bromide and 2.18 g of ethyl bromide are successively added under vigorously stirring. After 4 hours a further 1.09 g of ethyl bromide are added.

After 8 hours the organic layer is separated, washed with water, dried, evaporated in vacuo, and the oily residue constituted by 1,4-diethyl-5-carbobenzyloxy-4,5,6,7-tetrahydroimidazo-[4,5-c]-pyridine, Rf 0.54 in the system chloroform:methanol 9:1, and minor quantities of 3,4-diethyl-5-carbobenzyloxy-4,5,6,7-tetrahydroimidazo-[4,5-c]-pyridine, Rf 0.45 in the same system, is chromatographed on a silica gel column to give 4.8 g of 1.4-diethyl-5-carbobenzyloxy-4,5,6,7-tetrahydroimidazo-[4,5-c]-pyridine, (VIII':$R_1=R_2=C_2H_5$), oil.

MNR (CDCl$_3$): 1.05δ(t, CH$_3$—C(H$_2$)—C)
1.40δ(t, CH$_3$—C(H$_2$)—N)
3.86δ(q, C(H$_3$)—CH$_2$—N)
5.19δ(s, COOCH$_2$)
7.36δ(s, aromatic and imidazole protons).

This oil (A) is dissolved in 57 ml of 20% HBr in glacial acetic acid, and left to stand for 1 hour at room temperature. The solution is successively evaporated in vacuo and the residue dissolved in water; the aqueous solution, washed twice with ether, is evaporated to dryness. The solid residue is dissolved in 18 ml of 2N sodium hydroxide, and the solution is evaporated to dryness. The residue is taken up in chloroform, the separated sodium bromide is filtered off, and the filtrate dried and evaporated in vacuo to an oily residue.

Alternatively the oily residue (A) is dissolved in ethanol and hydrogenated at 30 p.s.i. and 55°–60° C. for 4–5 hours over Pd/C 10% as catalyst.

Evaporation of the solvent gives 1,4-diethyl-4,5,6,7-tetrahydroimidazo-[4,5-c]-pyridine, (IV':$R_1=R_2=C_2H_5$), oil.

NMR spectrum (CDCl$_3$): 1.05δ(t, CH$_3$—C(H$_2$)—C)
1.38δ(t, CH$_3$—C(H$_2$)—N)
1.95δ(s, NH)
3.86δ(q, C(H$_3$)—CH$_2$N)
7.35δ(s, imidazole proton).

This oil is dissolved in 27 ml of anhydrous acetonitrile and treated with 2.7 g of isopropyl isothiocyanate, refluxed for 7 hours, allowed to stand overnight at −15° C., and finally filtered to give 3.88 g of 1,4-Diethyl-5-(N-isopropylthiocarbamoyl)-4,5,6,7-tetrahydroimidazo-[4,5-c]-pyridine melting at 196° C.

NMR (DMSO-d$_6$): 0.93δ(t, CH$_3$—C(H$_2$)—C—4)
1.08δ(d, isopropyl CH$_3$)
1.23δ(t, CH$_3$—C(H$_2$)—N)
5.52δ(t, C—4—H)
7.44δ(s, C—2—H).

For reference purpose, the NMR spectrum of the known 3,4-diethyl-5-(N-isopropylthiocarbamoyl)-4,5,6,7-tetrahydroimidazo-[4,5-c]-pyridine is reported as:

0.89δ(t, CH$_3$—C(H$_2$)—C—4)
1.10δ(d, isopropyl CH$_3$)
1.30δ(t, CH$_3$—C(H$_2$)—N)
6.16δ(t, C—4—H)
7.45δ(s, C—2—H)

EXAMPLE 2

1-Methyl-4-ethyl-5-(N-isopropylthiocarbamoyl)-4,5,6,7-tetrahydroimidazo-[4,5-c]-pyridine.

Operating as in Example 1, but employing methyl iodide, 1-Methyl-4-ethyl-5-(N-isopropylthiocarbamoyl)-4,5,6,7-tetrahydroimidazo-[4,5-c]-pyridine is obtained in 76% yield, m.p. 186° C.

NMR (DMSO-d$_6$): 0.93δ(t, ethyl CH$_3$)
1.10δ(d, isopropyl CH$_3$)
3.46δ(s, CH$_3$—N)
5.55δ(t, C—4—H)
7.39δ(s, C—2—H).

For reference purpose, the NMR spectrum of the known 3-Methyl-4-ethyl-5-(N-isopropylthiocarbamoyl)-4,5,6,7-tetrahydroimidazo-[4,5-c]-pyridine is reported as:

0.90δ(t, ethyl CH$_3$)
1.12δ(d, isopropyl CH$_3$)
3.50δ(s, CH$_3$—N)
6.01δ(t, C—4—H)
7.27δ(s, C—2—H)

EXAMPLE 3

1-Methyl-5-(N-isopropylthiocarbamoyl)-4,5,6,7-tetrahydroimidazo-[4,5-c]-pyridine.

Operating as in Example 1, but starting from 4,5,6,7-tetrahydroimidazo-[4,5-c]-pyridine and employing methyl iodide, 1-Methyl-5-(N-isopropylthiocarbamoyl)-4,5,6,7-tetrahydroimidazo-[4,5-c]-pyridine is obtained in 75% yield, m.p. 200° C.

NMR (CDCl$_3$): 1.27δ(d, CH$_3$ isopropyl)

3.57δ(s, CH$_3$—N)
4.55δ(s, C—4—H$_2$)
7.38δ(s, C—2—H).

For reference purpose, the NMR spectrum of the known 3-Methyl-5-(N-isopropylthiocarbamoyl)-4,5,6,7-tetrahydroimidazo-[4,5-c]-pyridine is reported as:
1.25δ(d, isopropyl CH$_3$)
3.58δ(s, CH$_3$—N)
5.00δ(s, C—4—H$_2$)
7.38δ(s, C—2—H)

EXAMPLE 4

1-Methyl-5-(N-methylthiocarbamoyl)-4,5,6,7-tetrahydroimidazo-[4,5-c]-pyridine.

Operating as in Example 1, but starting from 4,5,6,7-tetrahydroimidazo-[4,5-c]-pyridine and methyl iodide, 1-Methyl-4,5,6,7-tetrahydroimidazo-[4,5-c]-pyridine is obtained as intermediate and successively reacted with methyl isothiocyanate to give 1-Methyl-5-(N-methylthiocarbamoyl)-4,5,6,7-tetrahydroimidazo-[4,5-c]-pyridine in a 78% yield, m.p. 238° C.

NMR (in D$_2$O of the hydrochloride):
2.81δ(t, C—6—H$_2$)
3.00δ(s, CH$_3$—NH)
3.78δ(s, CH$_3$—N—1)
4.12δ(t, C—7—H$_2$)
4.64δ(s, C—4—H$_2$)
8.46δ(s, C—2—H).

What is claimed is:
1. A compound of the formula (I):

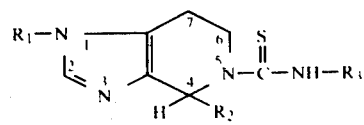

wherein R$_1$ is methyl or ethyl; R$_2$ is hydrogen or ethyl; and R$_3$ is methyl or isopropyl.

2. A compound as defined in claim 1, which is 1,4-Diethyl-5-(N-isopropylthiocarbamoyl)-4,5,6,7-tetrahydroimidazo-[4,5-c]-pyridine.

3. A compound as defined in claim 1, which is 1-Methyl-4-ethyl-5-(N-isopropylthiocarbamoyl)-4,5,6,7-tetrahydroimidazo-[4,5-c]-pyridine.

4. A compound as defined in claim 1, which is 1-Methyl-5-(N-isopropylthiocarbamoyl)-4,5,6,7-tetrahydroimidazo-[4,5,-c]-pyridine.

5. A compound as defined in claim 1, which is 1-Methyl-5-(N-methylthiocarbamoyl)-4,5,6,7-tetrahydroimidazo-[4,5-c]-pyridine.

* * * * *

UNITED STATES PATENT AND TRADEMARK OFFICE
CERTIFICATE OF CORRECTION

PATENT NO. : 4,223,146    Page 1 of 2

DATED : September 16, 1980

INVENTOR(S) : Giuliana Arcari; Luigi Bernardi; Giovanni Falconi; Ugo Scarponi

It is certified that error appears in the above-identified patent and that said Letters Patent are hereby corrected as shown below:

Column 3, formula VII should read as follows:

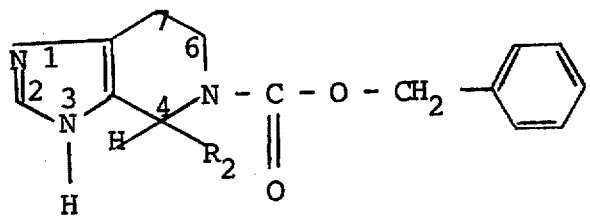

Column 5, formula I should read as follows:

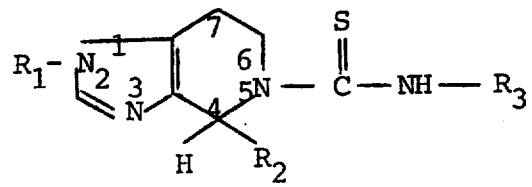

UNITED STATES PATENT AND TRADEMARK OFFICE
CERTIFICATE OF CORRECTION

PATENT NO. : 4,223,146
DATED : September 16, 1980
INVENTOR(S) : Giuliana Arcari, Luigi Bernardi; Giovanni Falconi; Ugo Scarponi It is certified that error appears in the above-identified patent and that said Letters Patent are hereby corrected as shown below:

Column 5, line 35, antagonist should read agonist

Signed and Sealed this

Eighteenth Day of August 1981

[SEAL]

Attest:

Attesting Officer

GERALD J. MOSSINGHOFF

Commissioner of Patents and Trademarks